United States Patent
Weinberg (10) Patent No.: US 9,622,809 B2
(45) Date of Patent: Apr. 18, 2017

(54) APPARATUS AND METHOD FOR SPATIALLY SELECTIVE INTERVENTIONAL NEUROPARTICLES

(71) Applicant: WEINBERG MEDICAL PHYSICS LLC, Bethesda, MD (US)

(72) Inventor: Irving N. Weinberg, Bethesda, MD (US)

(73) Assignee: Weinberg Medical Physics Inc, North Bethesda, MD (US)

(*) Notice: Subject to any disclaimer, the term of this patent is extended or adjusted under 35 U.S.C. 154(b) by 231 days.

(21) Appl. No.: 14/221,777

(22) Filed: Mar. 21, 2014

(65) Prior Publication Data

US 2014/0206927 A1    Jul. 24, 2014

Related U.S. Application Data

(63) Continuation-in-part of application No. 13/242,386, filed on Sep. 23, 2011, now abandoned.

(60) Provisional application No. 61/804,094, filed on Mar. 21, 2013, provisional application No. 61/810,436, (Continued)

(51) Int. Cl.
| | |
|---|---|
| *A61N 1/00* | (2006.01) |
| *A61B 18/12* | (2006.01) |
| *A61N 2/00* | (2006.01) |
| *A61B 18/18* | (2006.01) |
| *A61B 18/10* | (2006.01) |
| *A61M 5/142* | (2006.01) |
| *H01F 38/14* | (2006.01) |
| *A61N 1/378* | (2006.01) |
| *A61N 1/36* | (2006.01) |

(Continued)

(52) U.S. Cl.
CPC ........ *A61B 18/1206* (2013.01); *A61B 18/10* (2013.01); *A61B 18/18* (2013.01); *A61M 5/142* (2013.01); *A61N 1/36125* (2013.01); *A61N 1/3787* (2013.01); *A61N 1/37205* (2013.01); *A61N 2/00* (2013.01); *H01F 38/14* (2013.01); *H02J 50/10* (2016.02)

(58) Field of Classification Search
CPC .................... A61B 18/10–18/18; A61N 2/00
USPC ........................................................... 607/1
See application file for complete search history.

(56) References Cited

U.S. PATENT DOCUMENTS

| | | | |
|---|---|---|---|
| 2004/0015065 A1* | 1/2004 | Panescu ............... | A61B 5/0422 600/374 |
| 2004/0143296 A1* | 7/2004 | Wang .................... | A61M 21/00 607/2 |

(Continued)

OTHER PUBLICATIONS

Cadwallader; Gallium Safety in the Laboratory; Idaho National Engineering and Environmental Laboratory; 2003.

(Continued)

*Primary Examiner* — Amanda Patton
*Assistant Examiner* — Philip C Edwards
(74) *Attorney, Agent, or Firm* — Barnes & Thornburg LLP (57) ABSTRACT

An apparatus and method are provided for spatially-selective administration of actions by at least one device in the body using a transducer that is sensitive to a spatially-variant energy field imposed on the at least one device by a source external to a subject's body; and at least one component in the at least one device, wherein interaction of the transducer with the imposed spatially-variant energy field causes or enables at least one component in the at least one device to affect nearby tissues in the body.

24 Claims, 4 Drawing Sheets

Related U.S. Application Data filed on Apr. 10, 2013, provisional application No. 61/894,097, filed on Oct. 22, 2013.

(51) Int. Cl.
*A61N 1/372* (2006.01)
*H02J 50/10* (2016.01)

(56) References Cited

U.S. PATENT DOCUMENTS

2005/0058701 A1\* 3/2005 Gross ............... G01K 13/002
424/451
2007/0282378 A1\* 12/2007 Huang ............... A61N 1/3787
607/2

OTHER PUBLICATIONS

Cao et al.; Bi-Directional Micro Relays with Liquid-Metal Wetted Contacts; IEEE; 2005; pp. 371-374.

Chen et al.; Thermal and Hydrodynamic Characteristics of Constructual Tree-Shaped Minichannel Heat Sink; 2010; pp. 2018-22029; Vo. 56, No. 8.

Crump; Direct Digital Manufacturing Part One: What is Direct Digital Manufacturing; Fortus 3D Production Systems; 2009.

Knoblauch et al.; A Galinstan Expansion Femtosyringe for Microinjection of Eukaryotic Organelles and Prokaryotes; Nature Biotechnology; 1999; pp. 906-909; vol. 17.

Kolm; Hydromagnet: A Self-Generating Liquid Conductor Electromagnet; M.I.T. National Magnet Laboratory; 1961; pp. 1296-1304; vol. 32, No. 7.

Morley et al.; The MTOR LM-MHD Flow Facility, and Preliminary Experimental Investigation of Thin-Layer, Liquid Metal Flow in a I/R Toroidal Magnetic Field; Fusion Science and Technology; 2003; pp. 74-78; vol. 44.

Redinger et al.; An Ink-Jet-Deposited Passive Component Process for RFID; IEEE; 2004; pp. 1978-1983.

Urdaneta et al.; Goodbye Wires and Formers: 3-D Additive Manufacturing and Fractual Cooling Applied to MRI Gradient Coils.

\* cited by examiner

Figure 3

APPARATUS AND METHOD FOR SPATIALLY SELECTIVE INTERVENTIONAL NEUROPARTICLES

CROSS REFERENCE AND PRIORITY

The disclosure claims priority to and incorporates information previously described in U.S. Provisional Patent Application Nos. 61/810,436 (filed Apr. 10, 2013, and entitled "Neuroparticle"); 61/804,094 (filed Mar. 21, 2013, and entitled "Spatially-encoded Nanostimulator"); 61/894,097 (filed Oct. 22, 2013, and entitled "Neuroparticle"); and U.S. Nonprovisional patent application Ser. No. 13/242,386 (filed Apr. 19, 2012, and entitled "Flexible methods of fabricating electromagnets and resulting electromagnet elements").

FIELD

The disclosed embodiments relate to the use of nano- and micro-engineered electromagnetic devices to stimulate and/or sense the state of portions of the nervous system in vivo.

SUMMARY

Disclosed embodiments may be utilized to stimulate or otherwise affect portions of the nervous system of a subject's body without affecting other portions of the nervous system. The presently disclosed embodiments apply the principle of selecting zones magnetically to specify spatial locations in which very small circuits can be activated, and which once activated may stimulate, affect, and/or sense nearby tissues.

Although the term "stimulate" is used as an illustration of the mechanism for increasing the firing rate of neurons, it should be understood that the disclosed embodiments may also be used to decrease the firing rate of neurons (i.e., inhibit firing) by repeatedly stimulating neurons (e.g., by depleting stores of neurotransmitters) or by shorting electrical circuitry in neurons, or by heating nearby tissues, or electroporating nearby tissues, or through other neurophysiological means.

It should be understood that the effect on nearby tissues may be destructive, as would be desirable if the tissues were malignant or causing epilepsy or tremors to occur. In such a situation, the tissues affected might be other than neuronal tissues. The destruction could be immediate, or could result in long-term damage as might affect the ability of the cells to reproduce, or could potentiate other means of affecting tissues (e.g., by sensitizing tissue to subsequent radiation therapy).

In accordance with at least one disclosed embodiment an apparatus and method are provided for spatially-selective administration of actions by at least one device in the body using a transducer that is sensitive to a spatially-variant energy field imposed on the at least one device by a source external to a subject's body; and at least one component in the at least one device, wherein interaction of the transducer with the imposed spatially-variant energy field causes or enables at least one component in the at least one device to affect nearby tissues in the body.

BRIEF DESCRIPTION OF FIGURES

The presently disclosed embodiments will now be described in connection with one or more drawings, in which.

DETAILED DESCRIPTION

The present invention will now be described in connection with one or more contemplated embodiments. The embodiments discussed are not intended to be limiting of the scope of the present invention. To the contrary, the embodiments described herein are intended to be exemplary of the broad scope of the present invention. In addition, those skilled in the art will appreciate certain variations and equivalents of the embodiments described herein. The present invention is intended to encompass those equivalents and variations as well.

Disclosed embodiments may be utilized to stimulate or otherwise affect portions of the nervous system of a subject's body without affecting other portions of the nervous system. Although the term "stimulate" is used as an illustration of the mechanism for increasing the firing rate of neurons, it should be understood that the disclosed embodiments may also be used to decrease the firing rate of neurons (i.e., inhibit firing) by repeatedly stimulating neurons (e.g., by depleting stores of neurotransmitters) or by shorting electrical circuitry in neurons, or by heating nearby tissues, or electroporating nearby tissues, or through other neurophysiological means.

It should be understood that the effect on nearby tissues may be destructive, as would be desirable if the tissues were malignant or causing epilepsy or tremors to occur. In such a situation, the tissues affected might be other than neuronal tissues. The destruction could be immediate, or could result in long-term damage as might affect the ability of the cells to reproduce, or could potentiate other means of affecting tissues (e.g., by sensitizing tissue to subsequent radiation therapy).

It is known that energy may be transmitted inductively from a device located outside the body to a receiving device located in the body, as taught by Young-Sik Seo, Minh Quoc Nguyen, Zachariah Hughes, Smitha Rao, and J-C Chiao, in the article entitled "Wireless Power Transfer by Inductive Coupling for Implantable Batteryless Stimulators," presented at the 2012 International Microwave Symposium in Montreal Canada on Jun. 17-22, 2012 (incorporated herein by reference in its entirety). A small receiving device placed in the nervous system using such principles could therefore stimulate nearby tissues. Since the ability to focus Radio Frequency (RF) energy in a subject's body is limited to several centimeters (as shown in the 2004 Physical Review Letters article by B. E. Henty and D. D. Stancil, entitled "Multipath-Enabled Super-Resolution for RF and Microwave Communication Using Phase-Conjugate Arrays") (incorporated herein by reference in its entirety), multiple such receiving devices over a wide area would be activated or powered by the transmitter non-selectively. As a result, the stimulation scheme taught by Seo is limited in the ability to selectively affect small (e.g., sub-centimeter) portions of the nervous system without affecting other regions.

It is known that magnetic-field-free zones can be created in a body to impose spatial inhomogeneity, as taught by Bernard Gleich and Jürgen Weizenecker in an article entitled "Tomographic Imaging Using the Nonlinear Response of Magnetic Particles," published on Jun. 30, 2005 in the journal Nature, pages 1214-1217, volume 435 (incorporated herein by reference in its entirety). The system taught by Gleich was able to detect the location of magnetizable nanoparticles in a field-free-zone by sensing characteristic harmonic emanations from the magnetizable particles when exposed to radiofrequency waves. These emanations differed enough in field-free zones that the concentration of magnetizable particles in those field-free zones could be selectively differentiated from the concentration of particles in other zones (that were exposed to non-zero magnetic fields).

The presently disclosed embodiments apply the principle of selecting zones magnetically to specify spatial locations in which very small circuits can be activated, and which once activated may stimulate, affect, and/or sense nearby tissues. An enabling description of an example of such equipment and operation of the disclosed embodiments is provided as illustrated with FIGS. 1-4.

Figure 1:
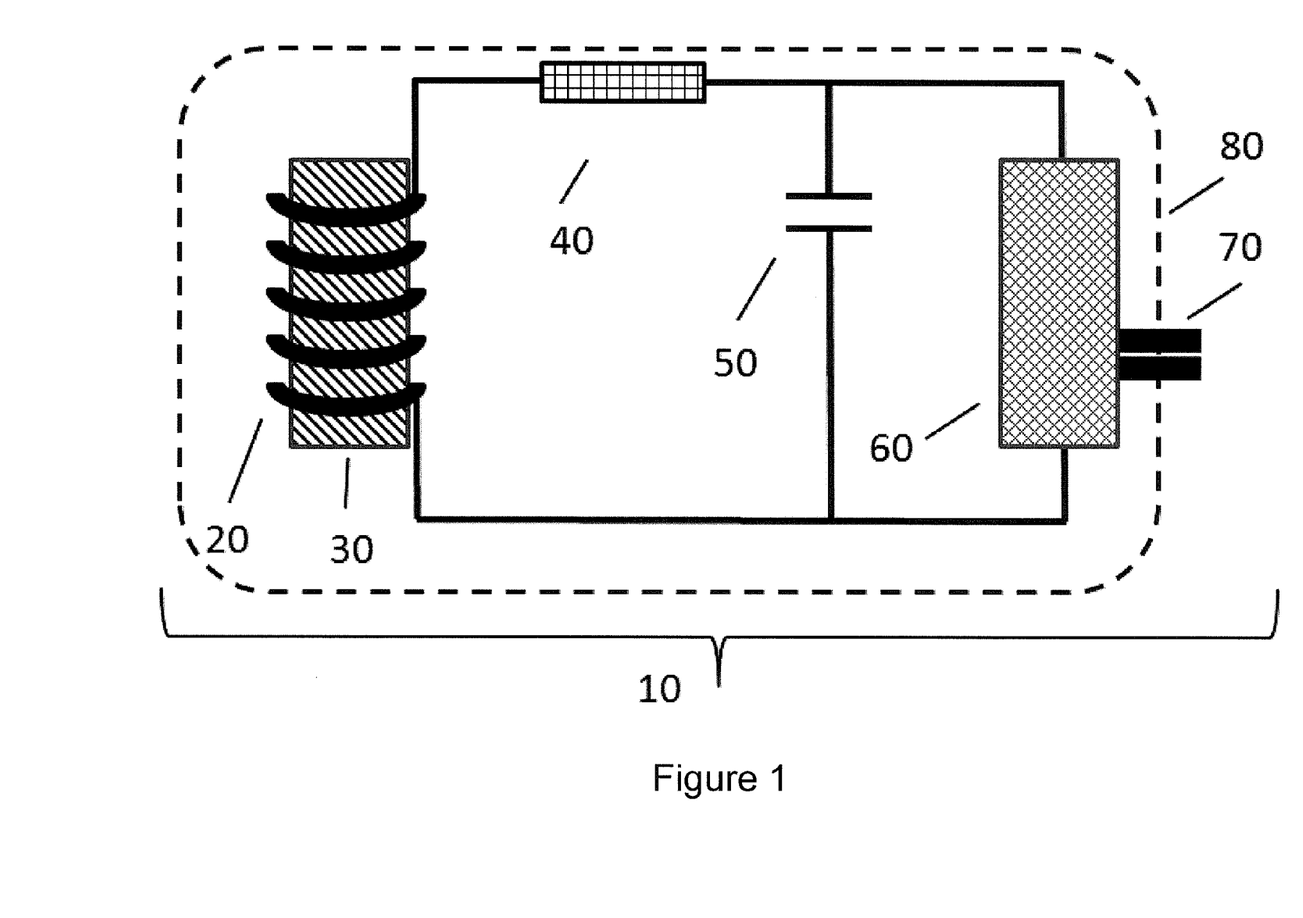
FIG. 1 illustrates one example of an electromagnetic device that will be provided to be resident in a nervous system and is part of an apparatus provided in accordance with the disclosed embodiments.

FIG. 1 illustrates one example of an electromagnetic device 10 that will be resident in a nervous system and is part of the disclosed embodiments. For the purposes of this description, the term "electromagnetic devices" includes but is not limited to devices that employ or are sensitive to electrical and/or magnetic energy, for example, spintronic devices or CMOS-fabricated circuits.

FIG. 1 shows an example of a small device 10 containing a transducer 20 that is near to or at least partially surrounds a core of magnetizable material 30. The transducer 20 of device 10, in combination with the core material 30, is capable of collecting energy transmitted by a transmission device 100 shown in FIG. 2.

In this example, the use of core 30, which will be unsaturated (and, therefore, support efficient collection of energy by device 10) only in the field-free region of magnetic field configuration 200, is sufficient to achieve selection of a region in which device 10 is activated. It should be understood that other magnetic configurations 200 could be used with other transducers 20 to achieve selection of one or more regions in which device 10 will be activated.

As illustrated in FIG. 1, device 10 includes a transducer 20, which converts ambient electromagnetic energy into electrical energy that can be stored or modified within the electromagnetic device 10. In FIG. 1, transducer 20 is represented by coil elements wound or otherwise placed around a magnetizable core 30, although other types of magnetic sensors (e.g., magnetostrictive, ferroelectric, magnetocapacitative, piezoelectric cantilever devices) could be used. It should be understood that the use of magnetic materials to move portions of mechanical generators (e.g., tribological generators) may also be included in the category of transducers.

Transducer 20 may be connected electrically through resistive and other circuit elements (for example, diodes) 40 to an energy storage device represented in FIG. 1 as a capacitor 50. Alternatively, transducer 20 may contain its own functional capacitance enabling it to store energy.

It should be understood that transducer 20 could be made sensitive to the magnetic field strength by other means than the saturation of core structure 30. For example, transducer 20 could be a giant magnetoresistance sensor that has been biased so as to only operate within a range of magnetic field strengths. It is understood that transducer 20 could be in a form that would be highly sensitive to electromagnetic radiation. For example, transducer 20 could be a ferroelectric cantilever in a spiral or other compact configuration, which would increase its effective length while preserving the overall small size of device 10.

Figure 3:
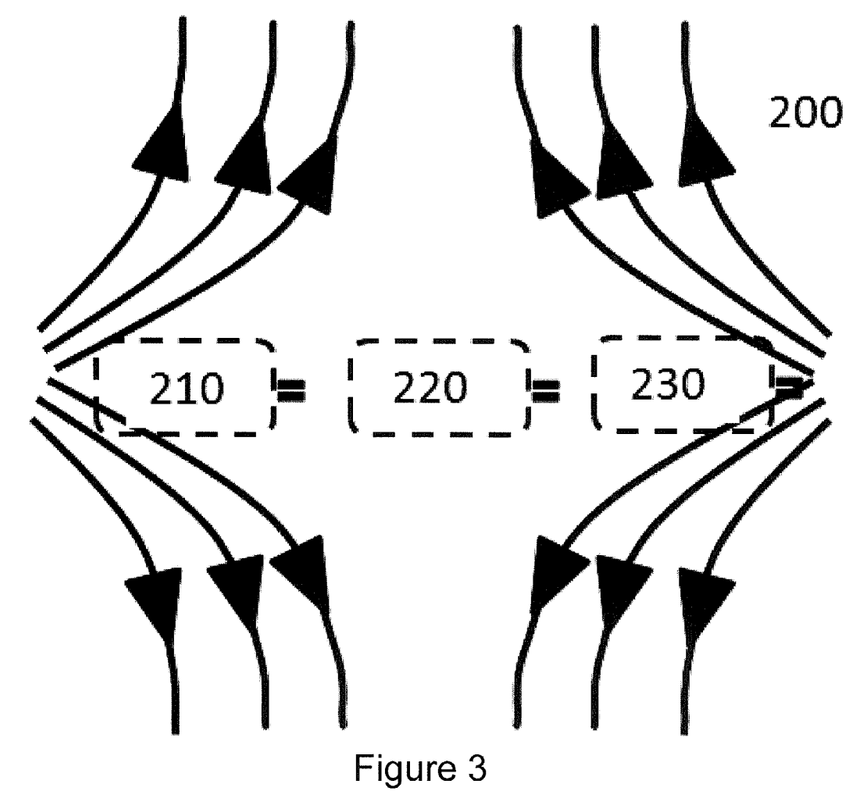
FIG. 3 is a representation of an enabling description of an example of the apparatus' magnetic field configuration, in which magnetic field 200 in the center of the configuration is below the saturation field for device core structure 30.

In the case where transducer 20 is not a coil around a core, but is, instead, a sensor of magnetic fields that is not saturated in a field-free region, device 10 might be active at a location where the field is higher, for example at 230 (see FIG. 3), rather than at a location where the field is minimal, for example at location 220 (see FIG. 3).

Energy from energy storage device 50 may be used to power or activate circuit 60, which may have antennae and/or contacts 70 that can be used as means to stimulate nearby tissue of a subject. Device 10 may be encapsulated by bio-compatible material 80, through which the electromagnetic effects of the stimulation means 70 can be transmitted, or through which at least some portion of means for stimulation (e.g., antennae) 70 may protrude.

The stimulating energy pulses or levels created by device 10 may be delivered to nearby tissues through the means to stimulate 70. To reduce the likelihood of ill effects in a subject's body, some or all of the portions of stimulating device 10 may be enclosed by a bio-compatible material 80. The electrodes, contacts in FIG. 1 are shown projecting through coating 80. It should be understood that the electrodes or antennae 70 may be within or on the surface of coating 80 and may still stimulate nearby tissues. For example, if the means 70 (e.g., antennae) were to deliver magnetic impulses to nearby tissues, the transmission of such pulses would be unhindered by a thin coating of bio-compatible 80.

The bio-compatible material 80 may have properties enabling it to effectively target or reside in certain cell types or in certain portions of cells. For example, if the bio-compatible material 80 is lipophilic, device 10 may, in one useful implementation, reside in a cell membrane of a neuron. Thus, portions of the means for stimulation (e.g., antennae) 70 may protrude into extracellular space or may penetrate into cells. Although the means for stimulation (e.g., antenna) 70 is illustrated as a single structure, it is understood that the means for stimulation 70 may be implemented using an assembly of one or more sensors, some of which may be in different locations within device 10 or remote to it.

The components and circuits shown in FIG. 1 may be utilized to utilize some of the energy harvested by transducer 20 to cause application of a stimulating pulse or series of pulses to tissues in the vicinity of device 10 and/or to sense the milieu of such tissues and emanate a signal reporting on these sensed values.

The process in which energy received by device 10 results in the application of pulses to nearby tissues can be of many types, an example of which is illustrated in FIG. 1. In that illustration, collected energy may be transferred through a resistive element and/or diode or other electronic component or power conditioning circuit 40 into a capacitor or other energy storage device 50. Power from the storage device 50 may then be applied to an oscillator circuit 60.

It should be understood that power conditioning circuitry 40 may include passive or active (e.g., diode) elements, placed at various locations in the main circuit, although for simplicity they are only shown at one location in FIG. 1. For example, several diodes in device 10 could be used to rectify an alternating current into direct current, as is well known in the field of electronic circuitry.

It should be understood that the oscillator circuit 60 can be replaced by some other circuit capable of creating appropriate pulses or static levels of electric or magnetic energy. Further, it should be understood that collected energy may be used to trigger an oscillating circuit that receives power from other means (e.g., an internal battery, a fuel cell harvesting energy from surrounding fluids, a piezoelectric element receiving energy from an ultrasonic beam, etc.).

The electromagnetic energy emitted from device 10 may be in the form of emitted light or heat that can affect cells in proximity to device 10. It should be understood that, instead of releasing electromagnetic energy, device 10 could use electrical or magnetic energy to release chemicals or other particulate matters (e.g., ions) from device 10 or from cells in proximity to device 10 into nearby tissues, or use electrical or magnetic energy to trigger or effect physical motion or deformation of device 10 or of cells in proximity to device 10 in ways that could affect nearby tissues.

In disclosed embodiments, the entire device 10 could be fabricated in very small dimensions, for example, less than a millimeter or micron in size, using nanotechnology methods that are known to practitioners of the art. As an example of such fabrication methods, the coil structure 20 illustrated in FIG. 1 could be wound upon the core 30, however in small dimensions such winding is not easy. However, such small dimensions (e.g., overall sizes that may be on the order of several microns or smaller), the winding of a coil may be affected through oblique angle deposition of conducting metal upon the core material, as taught by D-L Liu, D-X Ye, F. Khan, F. Tang, B-K Lim, R C Picu, G-C Wang, and T-M Lu, in the article entitled "Mechanics of Patterned Helical Si Springs on Si Substrate", published in 2003 in the Journal of Nanoscience and Nanotechnology, Vol. 3, Number 6, pages 492-495 (incorporated by reference in its entirety). Many windings of the coil structure may be accomplished with such methods, which may increase the voltage that can be collected from the ends of the coil structure.

It should be understood that transducers containing coil elements as shown in example by 20 in FIG. 1 may be implemented using deposits of conducting materials that are configured to conduct electrical currents. The deposition process may be in accordance with prior U.S. Non-Provisional patent application Ser. No. 13/342,386, entitled "Flexible Methods of Fabricating Electromagnets and Resulting Electromagnet Elements" (incorporated herein by reference in its entirety).

Figure 2:
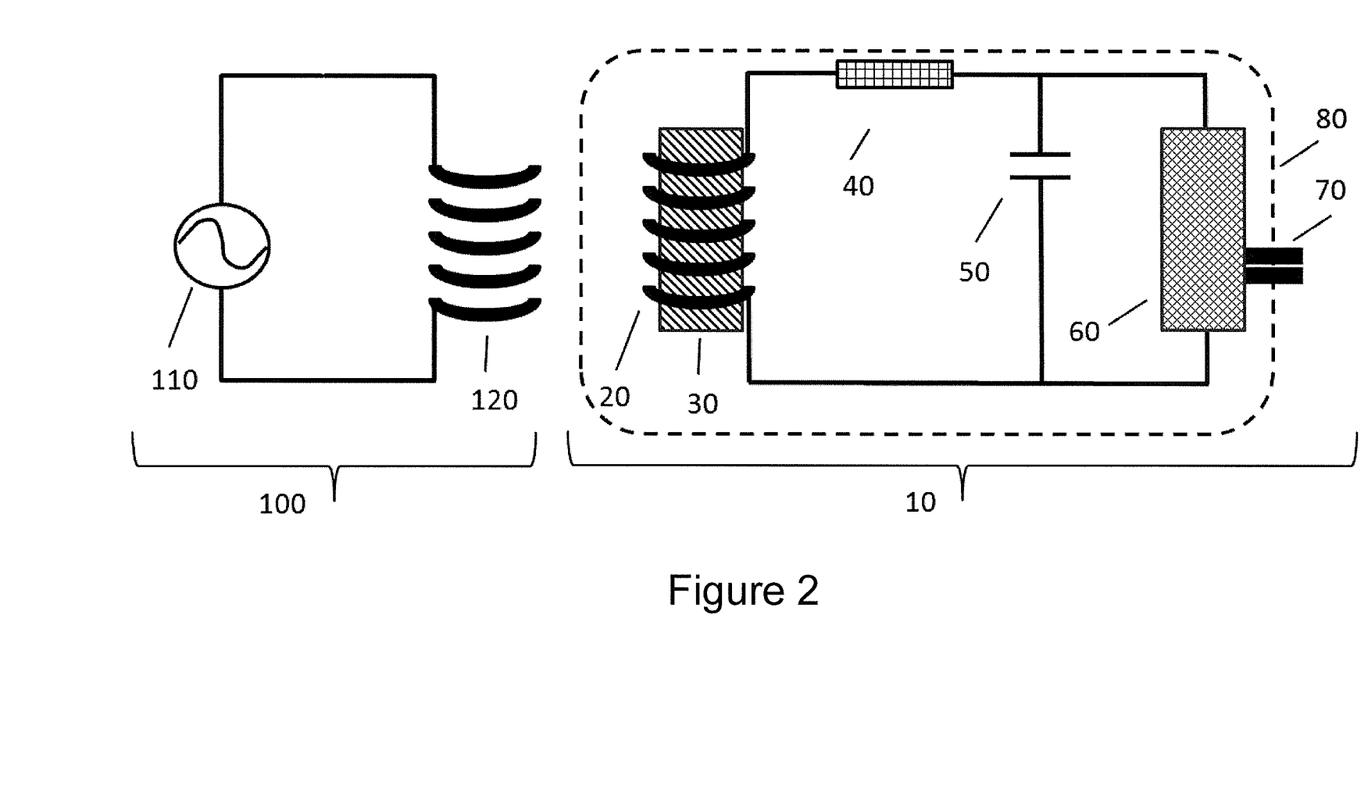
FIG. 2 illustrates transfer of energy from an energy transmitting device located outside of a subject's body into the device, illustrated in FIG. 1, and located in the subject's body in accordance with the disclosed embodiments.

FIG. 2 illustrates transfer of energy from a transmitting device 100 located outside of a subject's body into device 10 located within the subject's body. Transmitting device 100 includes a power supply 110 that delivers an oscillating or transient energy pulse to inductive coil and/or antenna 120. Power may be inductively transmitted through space from coil 120 to transducer 20.

It should be understood that both the transmitter 100 and device 10 may have more components and complexity than the representations of FIG. 2. It should also be understood that transmitting device 100 or a similar device may also, or alternatively, receive energy transmitted by device 10 located in a subject's body. Further, it should be understood that energy may be transmitted by device 10 located in a body to an antenna or sensor 120 outside of the subject's body.

In such cases, the energy could be used to elucidate or indicate the location of device 10 in the subject's body. For example, the frequency of the energy transmitted by device 10 could be a function of a magnetic field gradient applied to the subject's body by transmitting device 100 or other device external to the subject's body (e.g., a permanent magnet or electromagnet). Near-simultaneous transmission/reception on either the transmission device 100 or the internal device 10 could potentially be implemented using quarter-wavelength transmission lines as is customary in MRI circuits.

FIG. 3 is a representation of an enabling description of an example of the apparatus' magnetic field configuration, in which magnetic field 200 in the center of the configuration is below the saturation field for device core structure 30. Core structure 30 may be present in multiple electromagnetic devices 10.

Figure 4:
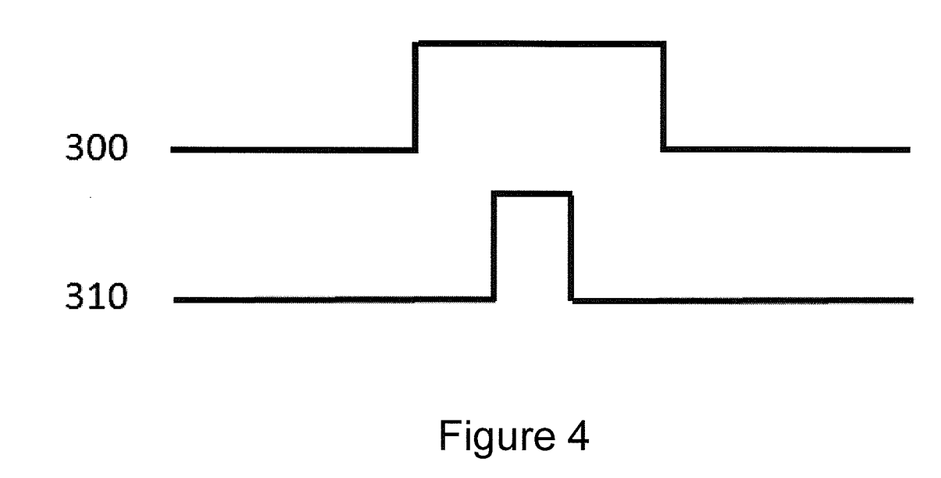
FIG. 4 is a representation of an enabling description of an example of the invention, in which a pulse sequence is applied by device 100.

In FIG. 3, devices 10 are represented as being in locations 210, 220, and 230 with respect to magnetic field 200. FIG. 4 (discussed below) illustrates that the device 10 located at position 220 is exposed to a low (or zero) magnetic field while the devices 10 located at positions 210 and 230 are exposed to significant magnetic fields.

Although FIG. 3 depicts a region of low field in the center of the region of interest, it should be understood that for operation of the device, the region of low magnetic field could be at another location within the region of interest.

In FIG. 3, devices 10 at locations 210 and 230 may be exposed to substantial magnetic fields, which saturate core material 30. For the purposes of this description, the term "saturate" is defined as a state in which the magnetization of the material no longer increases with increasing applied magnetic field. When core 30 is not saturated, it acts to increase the voltage induced in transducer 20 in response to transmitted RF oscillating field (310). If magnetic pulse (300) has saturated core 30, core 30 does not have the effect of increasing the signal in transducer 20 in response to transmitted RF oscillating field (310). If there is a non-zero relaxation time to the core material, pulse (300) may precede the transmitted oscillating field (310) instead of overlapping it as in FIG. 3. Thus we see that the temporary establishment of a field-free zone (i.e., in which pulse 300 is absent) improves the ability of transducer 30 to harvest energy.

It should be understood that the presence of a field-free zone can be achieved dynamically, for example as taught by P W Goodwill and S M Conolly in an article entitled "The X-Space Formulation of the Magnetic Particle Imaging Process: 1-D Signal, Resolution, Bandwidth, SNR, SAR, and Magnetostimulation", published in 2010 in the IEEE Transactions on Medical Imaging, Volume 29, number 11, pages 1851-1859 (incorporated herein by reference in its entirety).

However, is should be understood that the example of using saturation of core 30 to affect operation of device 10 is only one enabling example in which the operation of device 10 is affected by its position in a subject's body through the application of a magnetic field configuration 200. Many other approaches are possible in which the operation of device 20 could be affected by an externally-applied magnetic field configuration.

It should be understood that, if the magnetizable core 30 is not magnetically saturated, it can boost the effective length of the receiving transducer 20 by a significant factor (for example, a hundred-fold or more). In the example of a coil used as a transducer, the coil nature of receiving transducer 20 effectively increases the length of the transducer 20. Increasing the effective length of transducer 20 may permit more effective collection of electromagnetic radiation from the transmitter 100 at frequencies that pass through the skin.

The magnetizable core 30 may have the property that its magnetization saturates at some specific magnetic field strength, as is common for magnetizable materials (for example, iron oxides). As a result the transfer of energy from the transmission device 100 to the stimulation device 10 in FIG. 2 may be less effective when the device 10 is immersed in a magnetic field that is stronger than the saturation value than when the device 10 is immersed in a magnetic field that is weaker than the saturation value. Thus when one or more of device 10 is immersed in magnetic field configuration 200 (as illustrated in FIG. 3), certain locations of device 10 in the body will be relatively free of magnetic fields (e.g., position 220).

FIG. 4 is a representation of an example of a pulse sequence that may be applied by device 100. In this pulse sequence, a magnetic field magnitude 300 (an example of whose spatial configuration was shown as 200 in FIG. 3) is applied for a period of time to tissues in which one or more sets of electromagnetic device 10 reside. Within the time that the magnetic field 300 is applied, a RF or other electromagnetic pulse 310 may be sent to device 10 in the body by transmitter 100 (or by another transmitter) which is located outside the subject's body. In locations in the subject's body where the magnetic field 200 has a strength greater than the saturation field of the core 30, the RF pulse 310 will not effectively transfer energy to transducer 20. Such locations are shown as positions 210 and 230 in FIG. 3.

As a result of the poor transfer of energy to device 10 located at these positions, device 10 will not stimulate or otherwise affect tissues near those positions. It should be understood that the actual shape and sequence of pulses 300 and 310 may be substantially more complex than the representations shown in FIG. 4; however, the purpose of FIG. 4 meely illustrates that at least one constituent of pulse sequence 310 may occur coincidentally with the application of magnetic field 300.

A relevant aspect of the disclosed embodiment is that the magnetic environment that device 10 senses will affect its internal operation and subsequent activities. Thus, in this illustration of an example of the disclosed embodiments, the spatially-dependent saturation of core 30 is an example of a means of affecting the internal operation of device 10, where the spatial dependence is imposed through the application of magnetic field configuration 200 to a volume containing one or more of device 10.

For the purposes of the disclosed example, the magnitude of field strengths may be considered to be field-free if it is less than the saturation field of the core material 30 in the device 10. The magnetic field configuration 200 may be static or may be pulsed 300 as illustrated in the pulse diagram of FIG. 4.

Since magnetic core 30 in a field-free zone (such as position 220 of FIG. 3) is not saturated, core 30 is thus capable of reversible magnetization. In such a situation, energy can be effectively collected by devices 10 in field-free position 220 and cause stimuli to be delivered to tissues in the proximity of device 10. However, devices 10 in other positions (such as 210 and 230) may have their cores 30 saturated and be unable to collect energy, and thus may not deliver stimulating pulses to nearby tissues.

While this invention has been described in conjunction with the specific embodiments outlined above, it is evident that many alternatives, modifications and variations will be apparent to those skilled in the art. Accordingly, the various embodiments of the invention, as set forth above, are intended to be illustrative, not limiting. Various changes may be made without departing from the spirit and scope of the invention.

For example, as discussed above in the description of FIG. 3, it should be understood that transducer 20 could be made sensitive to the magnetic field strength and/or orientation by other means than the saturation of core structure 30. A general and relevant aspect of the disclosed embodiments is that the magnetic environment that device 10 senses will affect its internal operation and subsequent activities.

It should be understood that devices 10 may be transported through a subject's body and/or nervous system as a result of the application of magnetic gradients that may act on core material 30 or on other magnetizable materials within or attached to device 10. Such transportation is taught by I N Weinberg, M G Urdaneta, P Y Stepanov, D Beylin, A Nacev, A Sarwar, B Shapiro, O C Rodriguez, C Albanese, R Probst, and S T Fricke, in the article entitled "Non-invasive Image-Guided Brain Access with Gradient Propulsion of Magnetic Nanoparticles", published in the Proceedings of the 2012 IEEE Medical Imaging Conference (incorporated herein by reference in its entirety).

It should be understood that the device 10 can be used to determine the electrical and/or chemical milieu where it is located, through amplification of signals from the milieu obtained through antenna 70 and/or other sensors attached to device 10. Energy may be provided to device 10 through transmission from external coil 120 to transducer 20. Signals corresponding to the sensed milieu may be transmitted from the device 10 to an outside antenna 120 or to other sensors by transducer 20 or oscillating circuit 60 or other coils in device 10. Localization of device 10 in the body may be accomplished via the interaction of an external magnetic field with core material 30 and/or transducer 20.

Alternatively, or additionally to the use of the core material as a means of spatially-localizing the device in the body, the location and status (e.g., activation state) of device 10 in the body could be determined through comparison of signals emanating from 10 as sensed by external antennas 120 and/or components of antennas 120 or other sensing devices located at different positions and/or orientations with respect to device 10. Such comparison could include amplitude and/or phase of signals detected by external antennas or sensing devices. In addition, the use of focused RF (as described above) could potentially improve performance and/or spatial resolution when using the invention.

Devices 10 in a subject's body could detect the presence, location and/or state (e.g., activation status) of other such devices in the subject's body, for example using antennas 70.

The concentration of numbers of device 10 could be imaged through analysis of magnetization properties, as taught by Gleich, or by emission of energy from device 10 as described above. It is understood that magnetic pulses to affect such imaging, or to affect magnetic resonance imaging of the body, could be applied at different times from the pulses shown in FIG. 4, in order to implement image guidance.

It should be understood that a multitude of devices 10 could act within one or more regions of space, and at one or more times, to cause stimulation of nerve tissue.

It should be understood that disclosed embodiments may utilize a transducer that is sensitive to a spatially-variant energy field imposed on the at least one device by a source external to a subject's body; and at least one component in the at least one device, wherein interaction of the transducer with an imposed spatially-variant energy field causes or enables at least one component in the at least one device to affect nearby tissues in the body, for example, nearby tissues may be affected so as to potentiate subsequent application of another modality affecting the tissues. For example, since it is known that hot tissues are less able to tolerate radiation exposure than cool tissues, it is readily appreciated that heating cancerous tissues would render them more susceptible to radiation therapy. As another example, since it is known that radiation therapy kills cells as a result of multiple breaks in DNA, it is readily appreciated that causing initial breaks in DNA would render cells more susceptible to subsequent radiation therapy.

It should be understood that the above-disclosed embodiments and constituent equipment may be coupled to a computer processor that may be configured to output the image data and/or one or more graphical or image representations of that data to memory for storage and further analysis or reference at a later date. Further, the software code, instructions and algorithms utilized may be utilized by such a processor and may be stored in a memory that may include any type of known memory device including any mechanism for storing computer executable instructions and data used by a processor. Further, the memory may be implemented with any combination of read only memory modules or random access memory modules, optionally including both volatile and nonvolatile memory. Alternatively, some or all of the device computer executable instructions may be embodied in hardware or firmware (not illustrated). Further, it should be appreciated that, although not illustrated, the apparatus may similarly be coupled for communication and control to one or more user interfaces that may include display screens, one or more keyboards, and other types of user interface equipment.

As noted above, there are numerous variations and equivalents of the present invention that should be appreciated by those skilled in the art. The present invention is intended to encompass those equivalents and variations.

Additionally, it should be understood that the functionality described in connection with various described components of various invention embodiments may be combined or separated from one another in such a way that the architecture of the invention is somewhat different than what is expressly disclosed herein. Moreover, it should be understood that, unless otherwise specified, there is no essential requirement that methodology operations be performed in the illustrated order; therefore, one of ordinary skill in the art would recognize that some operations may be performed in one or more alternative order and/or simultaneously.

Various components of the invention may be provided in alternative combinations operated by, under the control of or on the behalf of various different entities or individuals.

Further, it should be understood that, in accordance with at least one embodiment of the invention, system components may be implemented together or separately and there may be one or more of any or all of the disclosed system components. Further, system components may be either dedicated systems or such functionality may be implemented as virtual systems implemented on general purpose equipment via software implementations.

As a result, it will be apparent for those skilled in the art that the illustrative embodiments described are only examples and that various modifications can be made within the scope of the invention as defined in the appended claims.

What is claimed:

1. An apparatus for spatially-selective administration of an action by at least one device positioned inside a subject's body, the apparatus comprising:

at least one device positioned inside the subject's body including a transducer sensitive to a spatially-variant energy field imposed by a source external to the subject's body, and at least one component coupled to the transducer and configured to affect tissue positioned nearby the at least one component in the subject's body in response to the transducer reacting to the imposed spatially-variant energy field, wherein the spatially-selective administration of the action is performed by the at least one device as a function of the spatially-variant energy field applied to the subject's body.

2. The apparatus of claim 1, wherein the imposed spatially-variant energy field is an electromagnetic field.

3. The apparatus of claim 1, wherein the nearby tissues include neurons.

4. The apparatus of claim 1, wherein the nearby tissues are stimulated, inhibited, or heated.

5. The apparatus of claim 1, wherein the nearby tissues are damaged so that the tissues can no longer reproduce.

6. The apparatus of claim 1, wherein the nearby tissues are damaged so that the tissues can no longer survive.

7. The apparatus of claim 1, wherein the nearby tissues are affected so as to potentiate subsequent application of another modality affecting the tissues.

8. The apparatus of claim 1, wherein the effect on the nearby tissues is implemented through the application of electrical energy, application of magnetic energy, application of light, application of heat, or application of kinetic energy.

9. The apparatus of claim 1, wherein the effect on the nearby tissues is implemented through contortion of the at least one device or of a cell in proximity to or containing the at least one device.

10. The apparatus of claim 1, wherein the effect on the nearby tissues is implemented through the release of chemicals or other particulate matters.

11. The apparatus of claim 1, wherein the transducer is coupled to a magnetizable material.

12. The apparatus of claim 1, wherein the transducer uses the magnetoresistive effect, the magnetocapacitative effect, the ferroelectric effect, or the triboelectric effect.

13. The apparatus of claim 1, wherein the transducer is a cantilever.

14. The apparatus of claim 1, wherein the transducer is in a spiral configuration or a compact configuration.

15. The apparatus of claim 1, wherein the transducer harvests energy from an electromagnetic field imposed on the device by the source external to the subject's body.

16. The apparatus of claim 1, wherein the activation of the at least one device depends on its local milieu.

17. The apparatus of claim 1 wherein the at least one device is encapsulated in a biocompatible material.

18. The apparatus of claim 1, wherein the transducer triggers the release of energy from another component in the device that harvests energy from a source external to the body.

19. The apparatus of claim 1, further comprising a spatially-variant energy field source positioned external to the subject's body.

20. The apparatus of claim 1, wherein the largest dimension of the at least one device is less than one millimeter.

21. The apparatus of claim 1, wherein the spatial variance is the magnetic field gradient.

22. The apparatus of claim 1, wherein the spatial variance of the spatially-variant energy field is associated with a specific location with the subject's body.

23. An apparatus for spatially-selective administration of actions by at least one device in the body, the apparatus comprising:
- a transducer that is sensitive to a spatially-variant energy field imposed on the at least one device by a source external to a subject's body,
- and at least one component in the at least one device, wherein-interaction of the transducer with an imposed spatially-variant energy field causes or enables at least one component in the at least one device to affect nearby tissues in the body,
- wherein the transducer triggers the release of energy from another component in the device that harvests energy from a source external to the body.

24. An apparatus for spatially-selective administration of an action by at least one device positioned inside a subject's body, the apparatus comprising:
- at least one device positioned inside the subject's body including a transducer sensitive to a spatially-variant energy field imposed by a source external to the subject's body, and at least one component coupled to the transducer and configured to sense the milieu of tissues positioned nearby the at least one component in the subject's body in response to the transducer reacting to the imposed spatially-variant energy field,
- wherein the spatially-selective administration of the action is performed by the at least one device as a function of the spatially-variant energy field applied to the subject's body.

* * * * *